US008193808B2

(12) United States Patent
Fu et al.

(10) Patent No.: US 8,193,808 B2
(45) Date of Patent: Jun. 5, 2012

(54) OPTICALLY INTEGRATED BIOSENSOR BASED ON OPTICALLY DETECTED MAGNETIC RESONANCE

(75) Inventors: Kai-Mei Camilla Fu, Palo Alto, CA (US); Paul Edward Barclay, Palo Alto, CA (US); Raymond G. Beausoleil, Redmond, WA (US); Charles M. Santori, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 467 days.

(21) Appl. No.: 12/558,408

(22) Filed: Sep. 11, 2009

(65) Prior Publication Data

US 2011/0062957 A1 Mar. 17, 2011

(51) Int. Cl.
*G01V 3/00* (2006.01)
(52) U.S. Cl. ............................................. 324/304
(58) Field of Classification Search ........... 324/300–322
See application file for complete search history.

(56) References Cited

U.S. PATENT DOCUMENTS

| | | | | |
|---|---|---|---|---|
| 6,858,436 | B2 * | 2/2005 | Zenhausern et al. | 436/164 |
| 7,205,764 | B1 * | 4/2007 | Anderson et al. | 324/307 |
| 7,300,631 | B2 * | 11/2007 | Miller et al. | 422/82.01 |
| 7,564,245 | B2 * | 7/2009 | Lee | 324/321 |
| 7,648,844 | B2 * | 1/2010 | Srivastava et al. | 436/526 |
| 7,781,228 | B2 * | 8/2010 | Menon et al. | 436/526 |
| 7,843,567 | B2 * | 11/2010 | Moon et al. | 356/417 |
| 8,049,893 | B2 * | 11/2011 | Moon et al. | 356/417 |
| 8,102,176 | B2 * | 1/2012 | Lee | 324/309 |

OTHER PUBLICATIONS

Xu, Liang et al.; "Giant Magnetoresistive Sensors for DNA Microarray"; IEEE Transactions on Magnetics; Nov. 2008; vol. 44; No. 11.
Fu, Chi-Cheng et al.; "Characterization and application of single fluorescent nanodiamonds as cellular biomarkers"; PNAS; Jan. 16, 2007; pp. 727-732; vol. 104; No. 3.

Osterfeld, Sebastian J. et al.; "Multiplex protein assays based on real-time magnetic nanotag sensing"; PNAS; Dec. 30, 2008; pp. 20637-20640; vol. 105.; No. 52.
Tamanaha, C.R., et al.; "Magnetic labeling, detection, and system integration"; Biosensors and Bioelectronics; 2008; vol. 24; pp. 1-13.
Childress, L. et al.; "Coherent Dynamics of Coupled Electron and Nuclear Spin Qubits in Diamond"; Science; Oct. 13, 2006; vol. 314; pp. 281-285; American Association for the Advancement of Science; Washington DC.
Gruber, A. et al.; "Scanning Confocal Optical Microscopy and Magnetic Resonance on Single Defect Centers"; Science; Jun. 27, 1997; vol. 276; pp. 2012-2014; American Association for the Advancement of Science; Washington DC.
Li, Guanxiong et al.; "Spin valve sensors for ultrasensitive detection of superparamagnetic nanoparticles for biological applications"; Sensors and Actuators A; 2006; vol. 126; pp. 98-106.
Degen, C.L; "Scanning magnetic field microscope with a diamond single-spin sensor"; Applied Physics Letter; 2008; vol. 92.; pp. 243111-1 through 243111-3.
Taylor, J.M. et al.; "High-sensitivity diamond magnetometer with nanoscale resolution"; Natures Physics; vol. 4; Oct. 2008; pp. 810-816; Macmillan Publishers Limited.
Berman; Gennady P. et al.; "Single-Spin Microscope with Sub-Nanoscale Resolution Based on Optically Detected Magnetic Resonance"; http://arxiv.org/ftp/arxiv/papers/0905/0905.2361.pdf.
Barclay, Paul E. et al; "Microfiber Magnetometer"; U.S. Appl. No. 12/429,876, filed Apr. 24, 2009.

* cited by examiner

*Primary Examiner* — Dixomara Vargas (57) ABSTRACT

An optically integrated magnetic biosensor includes an optically detected magnetic resonance (ODMR) center and a fluidics layer configured to contain a solution comprising analytes, the fluidics layer being disposed over the ODMR center. A light source which generates incident light excites electrons within the ODMR center from a ground state to an excited state and a radio frequency (RF) antenna generates an RF field incident with frequencies which correspond to ground state transitions in the ODMR center. The ODMR center produces emitted light when illuminated by the incident light. The characteristics of the emitted light are influenced by the RF field and magnetic nanoparticles attached to the analytes. A method for detecting analytes using optically detected magnetic resonance is also provided.

20 Claims, 9 Drawing Sheets

OPTICALLY INTEGRATED BIOSENSOR BASED ON OPTICALLY DETECTED MAGNETIC RESONANCE

BACKGROUND

The ability to detect extremely small numbers of analytes can be useful in a variety of applications. For example, the detection of cancer-associated proteins, or biomarkers, in blood samples is a potentially powerful tool for early diagnosis of cancer and monitoring of cancer treatment. Additionally, ultrasensitive detection can aid in the identification of unknown biological material. In these and other applications, it could be desirable to perform very sensitive biomarker detection with very small volumes of biological samples.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

The ability to detect extremely small numbers of analytes can be valuable in a variety of applications. For example, the detection of cancer-associated proteins, or biomarkers, in blood samples is a potentially powerful tool for early diagnosis of cancer and monitoring of cancer treatment. Additionally, ultrasensitive detection can aid in the identification of unknown biological material. In these and other applications, it could be desirable to perform very sensitive biomarker detection with very small volumes of biological samples.

According to one illustrative embodiment, an optically detected magnetic resonance (ODMR) center can be used to detect magnetic nanotags which are selectively attached to biological molecules or other entities. ODMR centers are defects in a matrix material (typically a crystal lattice) whose magnetic energy levels can be detected optically. By sensing changes in light emitted from the ODMR centers, changes in external magnetic fields can detected. For example, nitrogen-vacancy (NV) centers in a diamond lattice are one type of ODMR center which can be used as an ultra-sensitive detector for magnetic nanotags. The detection of external magnetic fields by a nitrogen-vacancy center is accomplished using two unique properties of the nitrogen-vacancy center: the long-lived ground-state electron-spin coherence and the coupling of the electron spin state to optical transitions. When one or more magnetic nanotags are in proximity to the nitrogen-vacancy center, the optical behavior of the nitrogen-vacancy center is altered. This allows for very precise and sensitive detection of the biological molecules that are attached to the magnetic nanotags.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an embodiment," "an example" or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Throughout the specification a nitrogen-vacancy center within a diamond crystal lattice is used as an illustrative example of an optically detected magnetic resonance (ODMR) center. A number of other materials and centers which exhibit optically detected magnetic resonance could be used. For example, in a diamond lattice, silicon and nickel centers may exhibit optically detected magnetic resonance.

As used in the specification and appended claims, the term "functionalized" refers to an alteration of a surface such that a class of molecules selectively binds to the surface. For example, surfaces can be functionalized by attaching antibodies to the surface which preferentially bind to specific protein molecules. The type and number of antibodies can be varied across the surface to produce an array which simultaneously assays a number of different analytes.

Figure 1A:
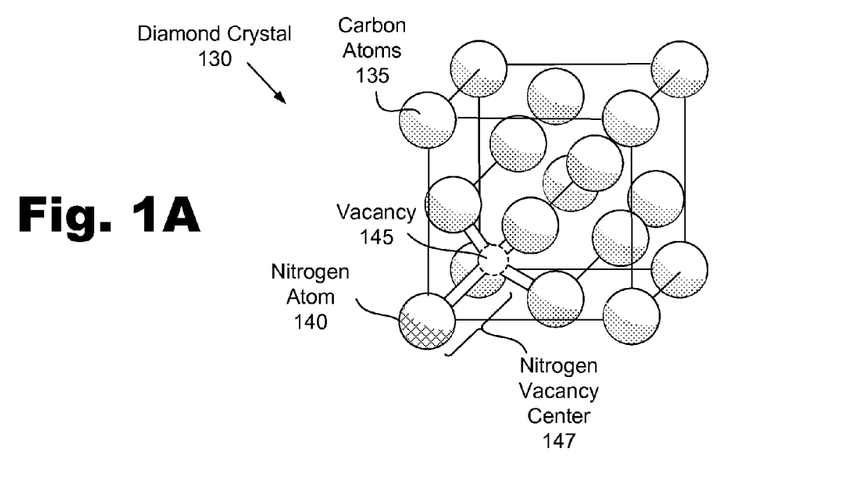
FIG. 1A is a diagram of an illustrative diamond crystal lattice containing a nitrogen-vacancy center, according to one embodiment of principles described herein.

FIG. 1A is an illustrative diagram of a nitrogen-vacancy center (147) within a diamond crystal lattice (130). The nitrogen-vacancy center (147) occurs when a nitrogen atom (140) is substituted for a carbon atom (135) and paired with an adjacent vacancy (145). According to one illustrative embodiment, these nitrogen-vacancy centers (147) can be produced by irradiation of diamonds by high-energy particles. For example, ion implantation techniques can be used to create vacancy centers (147) in diamonds. The diamond crystal or nanocrystal (130) can then be annealed at high temperatures to increase the mobility of the vacancies (145) within the crystal lattice. The vacancies (145) naturally move to pair with the nitrogen atoms (140), creating a nitrogen-vacancy center (147). However, in some commercially available industrial diamond nanocrystals the nitrogen-vacancy centers are already present as a result of the manufacturing process.

One property of nitrogen-vacancy centers (147) in a diamond lattice (130) is that the electrical state of electrons associated with the nitrogen-vacancy center (147) can be altered by a number of external stimuli. For example, the application of external optical energy, microwave energy, and magnetic fields all influence the behavior of the nitrogen-vacancy center.

Figure 1B:
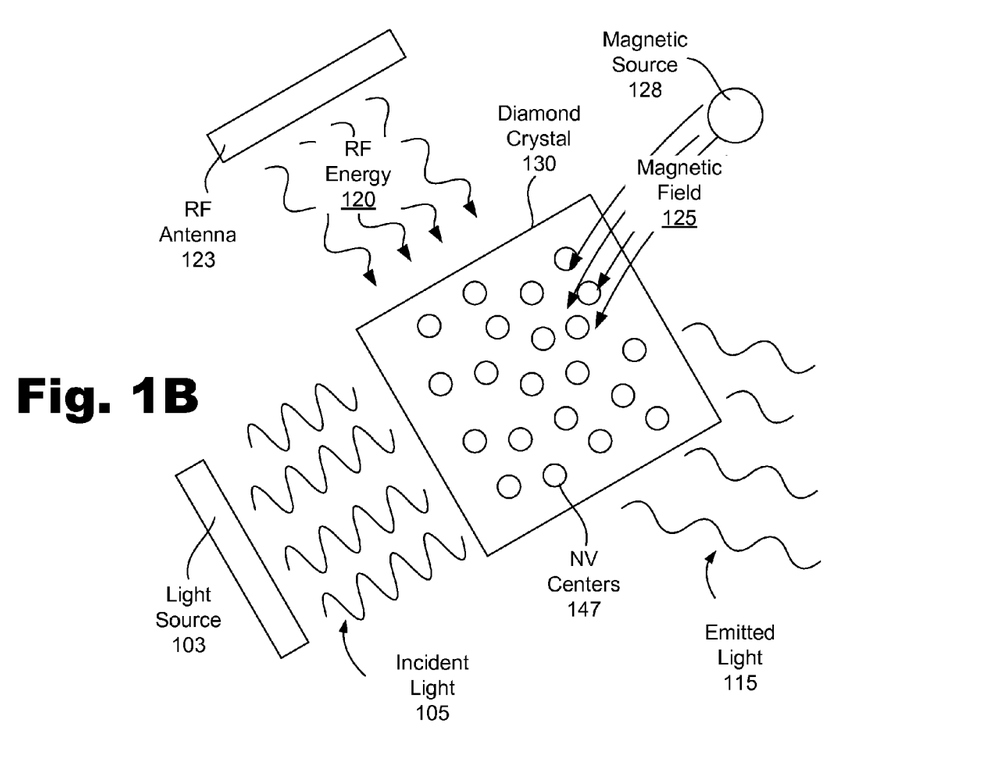
FIG. 1B is a diagram of illustrative interactions between a diamond crystal containing nitrogen-vacancy centers and externally applied electromagnetic fields, according to one embodiment of principles described herein.

FIG. 1B is a diagram of an illustrative diamond crystal (130) which includes optically detected magnetic resonance (ODMR) centers. The nitrogen-vacancy (NV) centers (147) can be sensitive to a variety of externally applied fields including radio frequency (RF) radiation (120), incident optical energy (105), and external magnetic fields (125). The externally applied fields can be generated by an RF antenna (123), a light source (103), and a magnetic source (128), respectively. Emitted light (115) having a characteristic wavelength and intensity is produced by the nitrogen-vacancy centers as a result of excitation of the NV centers (147) by the incident light (105).

According to one illustrative embodiment, the incident light (105) has a shorter and more energetic wavelength than the emitted light (115). The incident light (105) may be generated by a variety of optical sources (103), including light emitting diodes and lasers. The incident light (105) should have enough energy to excite relevant transitions between electron states but not so much energy that the nitrogen-vacancy center (147, FIG. 1A) is ionized. For example, if one is working with the negatively charged state of the nitrogen-vacancy center (147, FIG. 1A) in a diamond crystal (130), optical wavelengths between 480 nm and 638 nm have been found to have sufficient energy to excite the relevant transition(s) without producing a high rate of ionization. Light in this wavelength range can be produced by a number of lasers. By way of example and not limitation, the optical source may be a laser diode, argon laser, krypton laser, frequency doubled Nd:YAG laser, dye lasers, or He—Ne laser.

By controlling the application of incident light (105) and radio frequency (RF) energy (120), an externally applied magnetic field (125) can be detected by measuring the emitted light (115). Information about the magnitude of the magnetic field can be obtained by measuring the optical intensity as a function of the RF field's frequency.

Figure 1C:
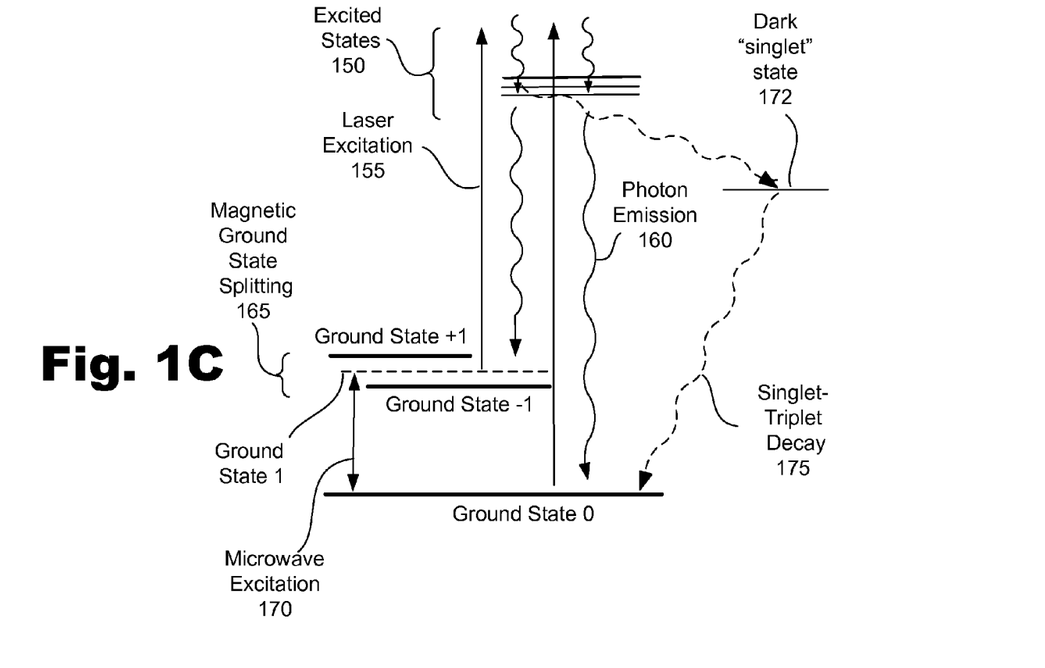
FIG. 1C is a diagram of illustrative electron states and transitions within a nitrogen-vacancy center, according to one embodiment of principles described herein.

FIG. 1C is an illustration of various electron energy states in a negatively charged NV center (147, FIG. 1B) and shows the influence of the incident light (105, FIG. 1B), the RF energy (120, FIG. 1B) and the externally applied magnetic field (125, FIG. 1B) on the electron behavior in the NV center (147, FIG. 1B).

The negatively charged state of the nitrogen-vacancy center (147, FIG. 1A) has three ground states: ground states 0, +1 and −1. At zero magnetic field, the +1 and −1 states are degenerate (they have the same energy). The application of an external magnetic field splits ground states +1 and −1 apart in energy. These ground states are labeled by their spin projections onto the nitrogen-vacancy axis. The characteristics of this magnetically induced shift can be dependent on a number of factors including the orientation and magnitude of the external magnetic field.

Radio frequency radiation, such as microwave radiation (170), can be generated by an antenna which is in close proximity to the nitrogen-vacancy center (147, FIG. 1A). For example, the microwave radiation (170) may be generated by metal leads which are attached to the sides of the diamond chip. Applying microwave radiation (170) to the nitrogen-vacancy center (147, FIG. 1A) causes a redistribution of the electron population between the ground states. The characteristics of this redistribution can depend on a number of factors including the frequency of the microwave radiation (170). According to one illustrative embodiment, the application of microwave radiation (170) with a frequency that is resonant with the energy difference between the ground state 0 and the ground states +1 or −1 causes a large redistribution of the population between ground state 0 and ground states +1, −1. The presence of a magnetic field changes this resonant frequency by shifting the ground states ±1 to new energy levels relative to ground state 0.

Application of light from a laser excitation source to the nitrogen-vacancy center (147, FIG. 1A) results in the optical excitation of a portion of the electrons into one or more excited states (150). The electrons quickly revert to one of the ground states by emitting a photon of a characteristic energy and wavelength, or through a non-radiative process. With a high probability, electrons excited from ground state 0 emit photons (160) by reverting to the same ground state 0. Electrons excited from ground state +1, −1 emit a photon with a lower probability when they revert to the ground state, and may instead become trapped for some time in a dark "singlet" state (172). The transition of the electrons from the dark "singlet" state (172) occurs via a non-radiative decay or emission of a very low energy photon. The decay from the dark "singlet" state (172) is shown as singlet-triplet decay (175). Significantly, no photon in the detected collection band (637-800 nm for NV centers) is emitted while the electrons are trapped in the dark "singlet" state, or during the decay (175) from the dark "singlet" state (172). As a result, transitions originating from the +1, −1 ground states exhibit relatively weak photoluminescence compared to transitions originating from the 0 ground state. These photon emissions (160) can be captured and sensed using a number of methods, providing a means by which the population of electron spins in the 0 state can be measured. By monitoring the photon emissions (160) in the presence of microwave excitations (170) applied at various frequencies, the presence of an exterior magnetic field can be detected.

To sense the presence, magnitude, and/or direction of a magnetic field, microwave radiation is swept through a frequency range. According to one illustrative embodiment, this frequency range roughly corresponds to the shifts in ground state resonant frequencies which would be expected to be produced by magnetic fields. When the microwave frequency does not correspond to the resonant frequency between ground state 0 and ground state −1, +1, the photo emission (160) is relatively bright because a larger portion of the electrons reside at ground state 0. The laser excitation boosts these electrons from ground state 0 to one of the excited states (150). As discussed above, this results in a relatively bright photon emission (160) as the electrons return to ground state 0. However, as the microwave radiation frequency passes through the resonant frequency, a large portion of the electrons is redistributed from ground state 0 to ground states +1, −1. This results in a drop in the overall luminescence generated by the nanocrystal because of the lower photoemission generated by the transition between the excited states (150) to the ground states +1, −1.

Consequently, to measure the magnetic field present at the nanocrystal, the nanocrystal is illuminated with an incoming photon flux and the microwave radiation is swept through a frequency range. The emitted light is monitored for a reduction in magnitude. This frequency at which the reduction in emitted light occurs corresponds to the resonant frequency between the ground state 0 and the ground states +1 or −1. Any change in this frequency from a nominal value can be interpreted as a magnetically induced resonant frequency shift. The application of the appropriate calibration equation(s) then produces an estimation of the external magnetic field at the location of the nitrogen-vacancy centers (147, FIG. 1A).

In one example, when NV centers are excited by green light (532 nm, for example), their electron spins become polarized into the $m_s=0$ state. As discussed above, this spin polarized state produces a brighter photoluminescence signal in the 637-800 nm band under continued optical excitation at 532 nm. However, if sufficient RF microwave excitation is applied resonant with the $m_s=0 \rightarrow m_s=+/-1$ transitions at ~2.88 GHz, the optically induced spin polarization is destroyed, leading to a ~5-30% drop in the photoluminescence intensity. In the presence of a DC magnetic field, the $m_s=+/-1$ levels split, the RF excitation is no longer on resonance, and the photoluminescence intensity increases. The resulting ODMR spectrum can be analyzed to detect the presence of external magnetic fields.

Figure 1D:
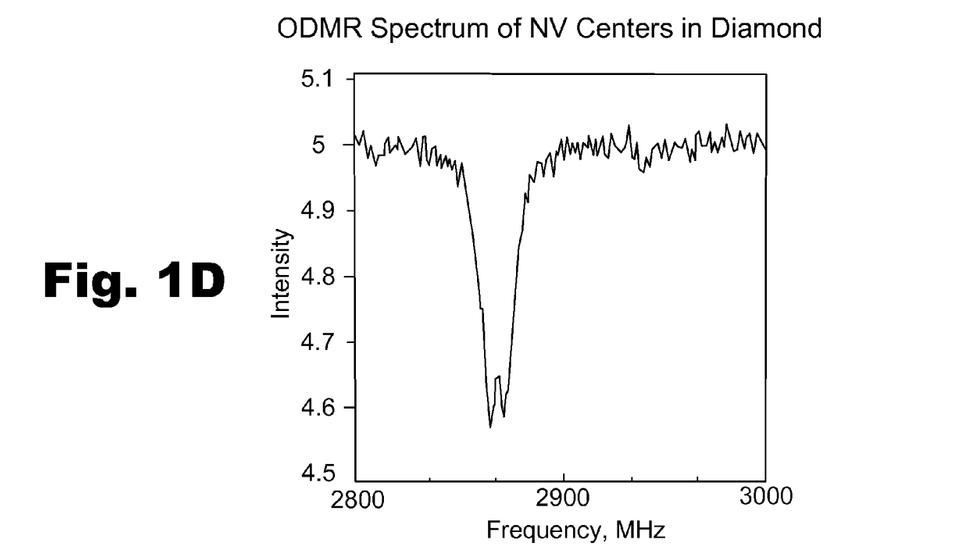
FIG. 1D is a graph of an illustrative optically detected magnetic resonance spectrum of nitrogen vacancies in diamond, according to one embodiment of principles described herein.

FIG. 1D shows the optically detected magnetic resonance (ODMR) spectrum of nitrogen-vacancy centers in diamond. The vertical axis of the graph shows the intensity of the emitted light and the horizontal axis of the graph shows the frequency of the applied radio frequency energy. As shown in the graph, when the applied RF energy frequency is on resonance with either the $m_s=0 \leftrightarrow m_s=+1$ or $m_s=0 \leftrightarrow m_s=-1$ transitions the fluorescence intensity decreases, producing two dips in the ODMR spectrum with a splitting proportional to the $m_s=+/-1$ level spacing. By measuring either the absolute position or the splitting of the ODMR dips, the magnetic field component parallel to the NV axis can be determined.

Additionally or alternatively, the microwave radiation frequency may be fixed on a resonance generated by a background magnetic field, effectively minimizing the photon emission from this field. Small magnetic field fluctuations from this background magnetic field will then produce increased photoemission and can then be measured by monitoring the change in photon flux at the fiber output. As a further alternative, a feedback circuit may be used to maintain the microwave radiation frequency close to a resonance such that the slope (the first derivative of the photoemission intensity with respect to the magnetic field intensity) is maximized, in order to maximize the signal-to-noise ratio of the magnetometer.

Figure 2A:
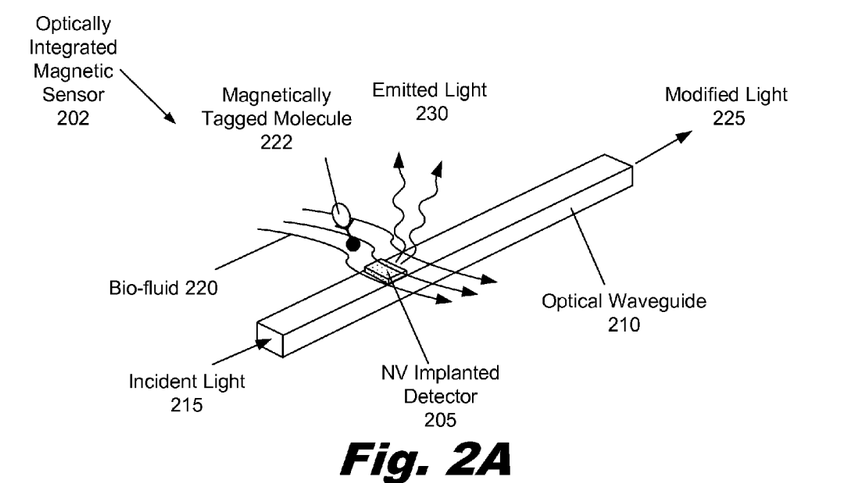
FIG. 2A is a diagram of an illustrative system for detecting magnetic bio-tags using a nitrogen-vacancy implanted sensor, according to one embodiment of principles described herein.

FIG. 2A shows an illustrative optically integrated magnetic sensor (202). According to one illustrative embodiment, the optically integrated magnetic sensor (202) includes a nitrogen-vacancy implanted diamond detector (205) attached to an optical waveguide (210). Incident light (215) is passed through the optical waveguide (210). A portion of the light (215) is incident on the nitrogen-vacancy implanted diamond (205) and excites electrons within the vacancies from a ground state to one or more excited states. As discussed above, the electrons revert back to the ground state by emitting photons (160, FIG. 1C). These photons (160, FIG. 1C) may be sensed as emitted light (230). Alternatively, a portion of the photons (160, FIG. 1C) may be coupled into the optical waveguide (210) and be conveyed through the waveguide as modified light (225). Consequently, the photons emitted by the NV implanted detector (205) may be sensed by an external sensor which detects the emitted light (230) or by a sensor which is optically connected to the waveguide (210) that could detect the modified light (225).

As discussed above, the optical output of the nitrogen-vacancy implanted detector (205) is sensitive to both RF energy and external magnetic fields. The exterior RF energy may be modulated to sense the presence or absence of external magnetic fields in proximity to the nitrogen-vacancy implanted detector (205). According to one illustrative embodiment, the nitrogen-vacancy implanted detector (205) may sense magnetically tagged molecules (222) within a bio-fluid (220). According to one illustrative embodiment, the magnetically tagged molecules (222) may include a biological molecule which is tagged with a magnetic tag which has a size of 20 nanometers or less. As the magnetically tagged molecules (222) approach the nitrogen-vacancy implanted detector (205), magnetic ground state splitting is induced. The modulated RF energy is then used to detect the resulting shift in the ODMR spectrum of the emitted photons.

This magnetic sensing can either work for time constant or time varying magnetic fields. For time constant fields, ferromagnetic particles can be detected with a sensitivity which can be limited by the spin dephasing time of the NV centers. Alternatively, paramagnetic particles in a DC bias field could be used.

For time changing magnetic fields, paramagnetic particles can be detected with a sensitivity which can be limited by the spin decoherence time of the NV centers and may result in sensitivities which are 10-100 times greater than for time constant magnetic fields. For example, a single 16 nm superparamagnetic nanoparticle with a magnetic moment of $10^{-15}$ emu positioned 0.2 μm above the sensing surface and magnetized along the z-axis may produce an average magnetic field of ~15 μT over a 0.5 μm diameter pixel at the location of the NV layer, and can in theory be detected unambiguously in 10 ms. Additionally, in a time varying mode it may be possible for the sensor (202) to distinguish between multiple magnetic nanotags which have sufficiently different magnetic moments.

Figure 2B:
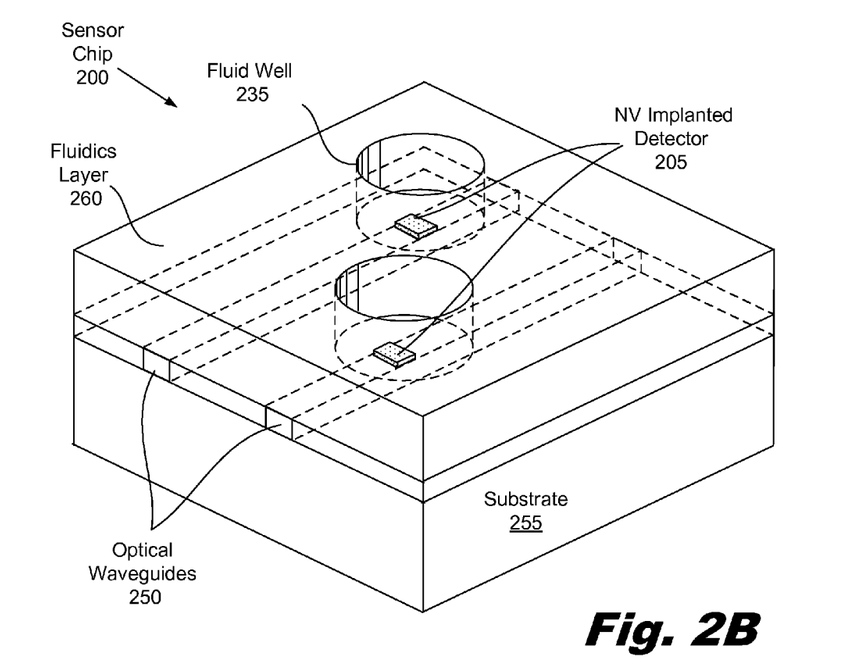
FIG. 2B is a perspective view of an illustrative optically integrated magnetic sensor, according to one embodiment of principles described herein.

FIG. 2B is a perspective view of an illustrative sensor chip (200) which includes elements of the optically integrated magnetic sensor (202, FIG. 2A) described above. According to one illustrative embodiment, the sensor chip (200) includes a substrate (255). A number of optical waveguides (250) are disposed on the upper surface of the substrate (255). The nitrogen-vacancy implanted diamond detectors (205) are formed on the optical waveguides (250) so that the detectors (205) are in optical communication with waveguides (250).

A fluidics layer (260) is formed over the optical waveguides (250). According to one illustrative embodiment, the fluidics layer (260) may form a number of fluid wells (235). The fluid wells (235) are designed to contain a volume of fluid in proximity to the nitrogen-vacancy implanted detectors (205). Embedded NV-rich diamond nanoparticles could be used for these detectors. According to one illustrative embodiment, the fluid wells (235) may have a size and layout which is compatible with conventional assay equipment. The fluidics layer may be formed from a variety of materials including biocompatible polymer materials such as polydimethylsiloxane (PDMS) or epoxy based polymers such as SU-8 photoresist. In some embodiment, the fluidics layer (260) may be formed using photolithographic techniques.

This configuration may have a number of advantages. For example, this configuration provides very close contact between the fluid and the diamond sensor. This increases the sensitivity by decreasing the distance between the magnetically tagged molecules and the nitrogen vacancies. Additionally, there is no need for additional free space optics. The excitation light (215, FIG. 2A) and emitted light (230, FIG. 2A) can be sensed through the optical waveguides (250). Although the sensor chip (200) is compatible with a variety of free space optical designs (such as those illustrated in FIGS. 4 and 5), the optical waveguides (250) may provide a smaller and more robust method of transmitting excitation light to the detectors (205) and sensing the emitted light generated by the detectors (205).

Figure 3:
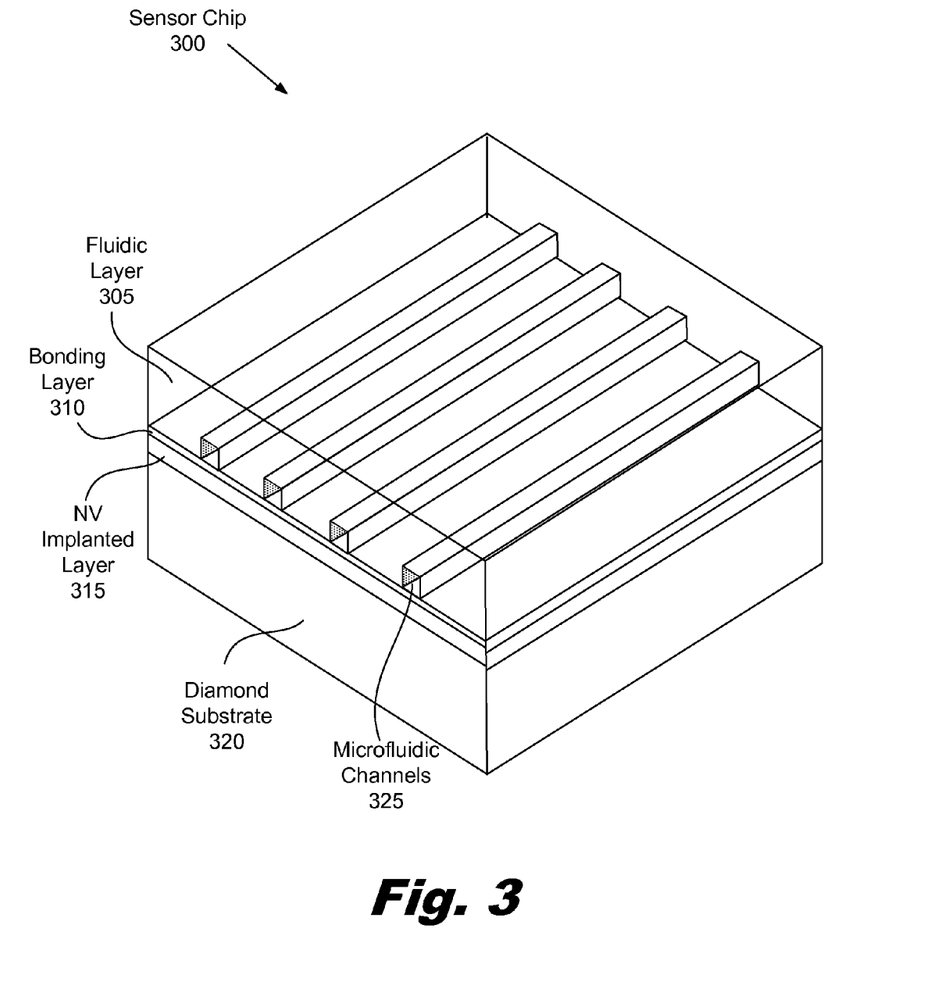
FIG. 3 is a perspective view of an illustrative optically integrated magnetic sensor, according to one embodiment of principles described herein.

FIG. 3 shows an alternative embodiment of a sensor chip (300) which includes an optically integrated magnetic sensor. In this illustrative embodiment, a diamond substrate (320) forms the base of the sensor. The diamond substrate may be natural, formed by chemical vapor deposition (CVD) or high pressure high temperature (HPHT) techniques. The upper portion of the diamond substrate (320) is a nitrogen-vacancy implanted layer (315). As discussed above, the NV implanted layer (315) may be made by ion implantation and annealing. The fluidic layer (305) is formed separately and bonded to the upper surface of the nitrogen-vacancy implanted layer (315) using a bonding layer (310). In this embodiment, the bonding layer is configured such that the fluidic layer (305) can be stripped or peeled from the underlying diamond substrate (320) after use. A new fluidic layer can then be bonded to the substrate.

The fluidic layer (305) includes a number of microfluidic channels (325) which contain and direct fluid over the implanted layer (315). The microfluidic channels (325) may be entirely contained within the fluidic layer (305) or may be formed as grooves in the lower surface of the fluidic layer (305). When the microfluidic channels (325) are formed as grooves in a surface of the fluidic layer (305), the bonding layer (310) forms a fourth surface of the channel. This configuration may minimize the distance between magnetic tags contained within the fluidic layer (305) and the nitrogen-vacancy centers in the NV implanted layer (315).

Additionally or alternatively, microfluid channels can be etched or otherwise formed within the diamond substrate itself. Although this may increase the fabrication costs, the channels within the diamond are extremely chemically and mechanically robust. Additionally, the fluid passing through the microchannels would be extremely close to the NV centers in the diamond substrate. The surfaces of the diamond channels can be directly functionalized, cleaned and refunctionalized. This allows for the repeated use of the device.

Figure 4:
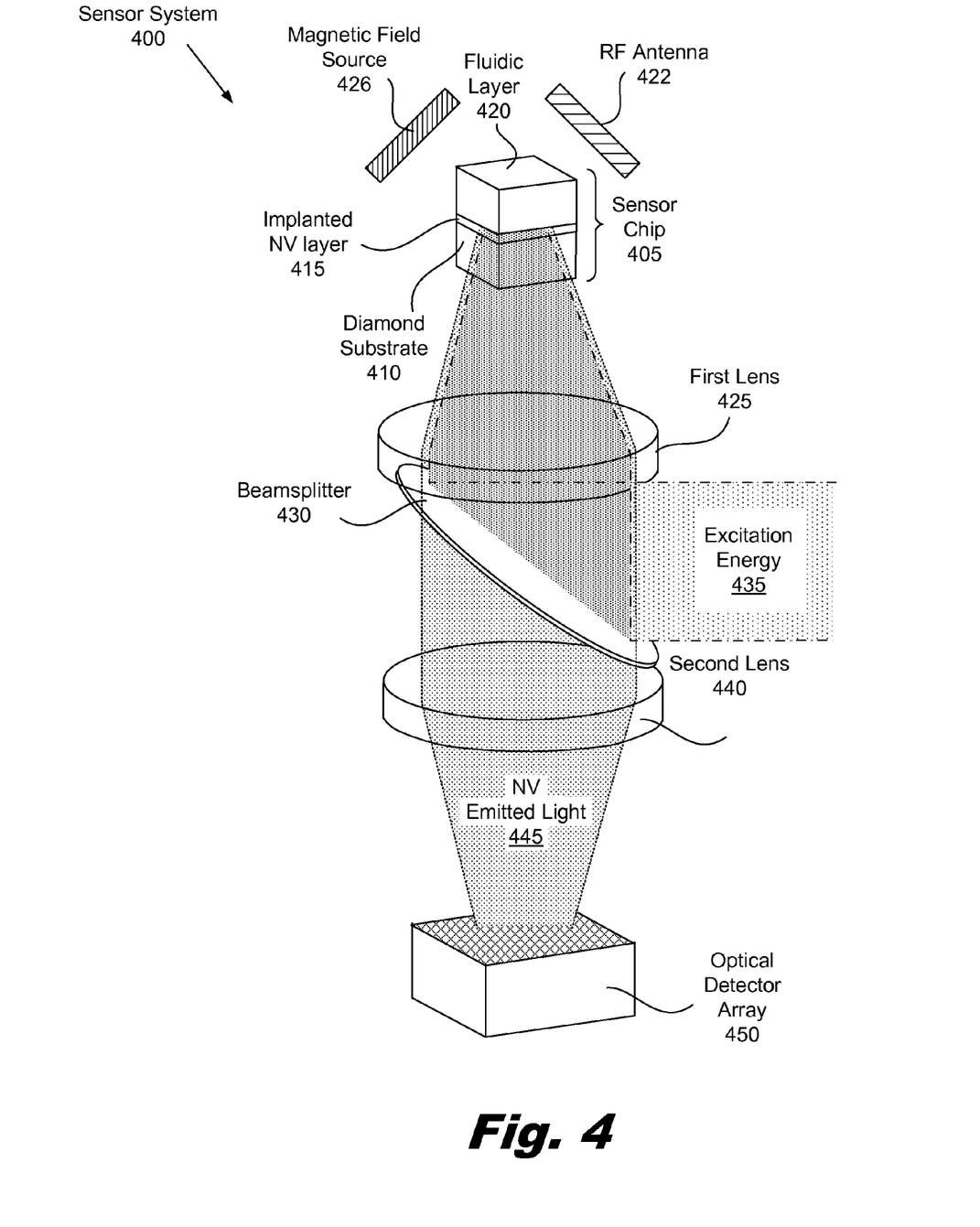
FIG. 4 is diagram of an illustrative sensor system which incorporates an optically integrated magnetic sensor, according to one embodiment of principles described herein.
Figure 5:
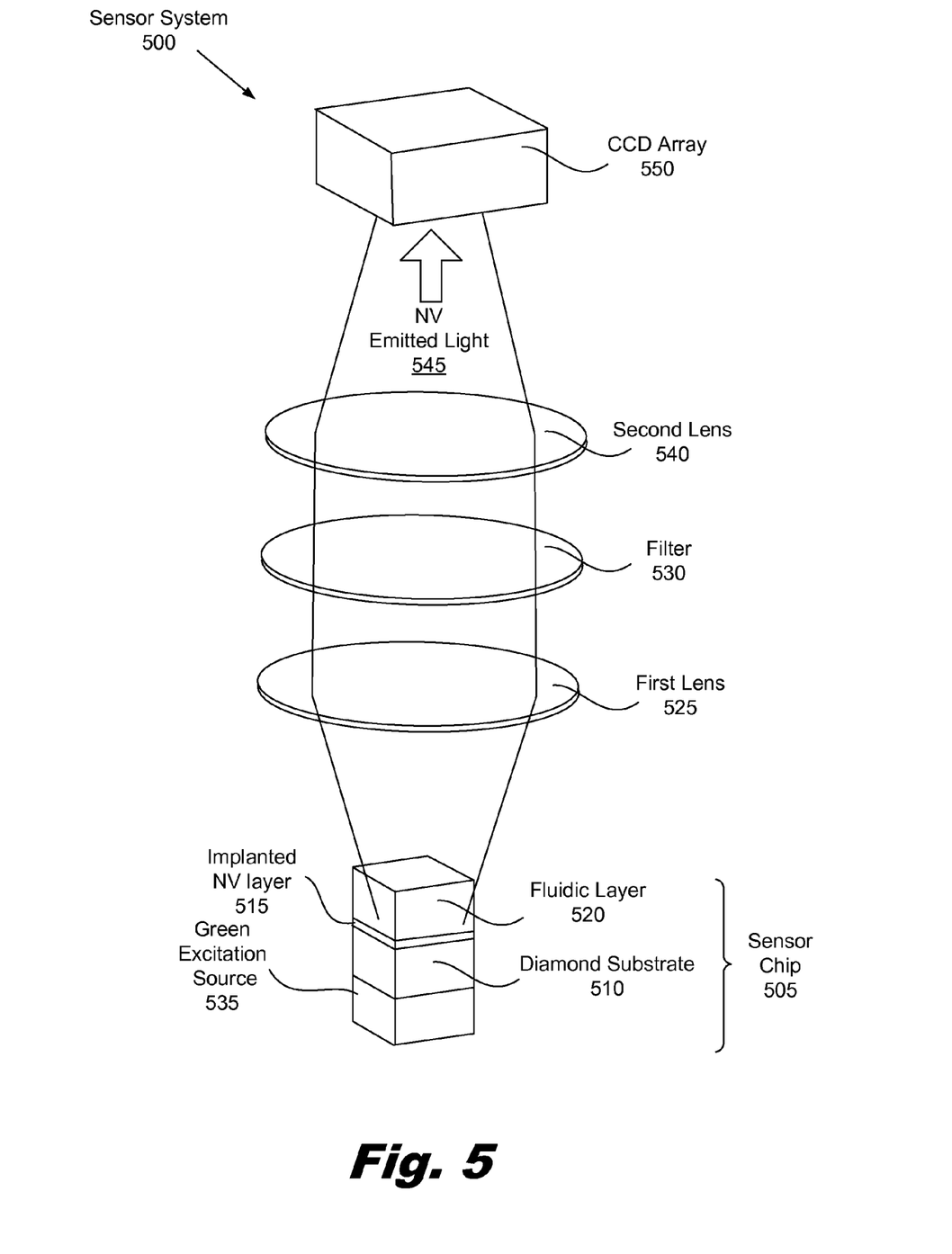
FIG. 5 is a diagram of an illustrative sensor system which incorporates an optically integrated magnetic sensor, according to one embodiment of principles described herein.

FIGS. 4 and 5 show two illustrative sensor systems which could be used to excite and image the optical emissions from nitrogen-vacancy centers. According to one illustrative embodiment shown in FIG. 4, the sensor chip (405) includes a diamond substrate (410) which forms a robust and transparent base for the chip. The implanted nitrogen-vacancy layer (415) is formed over the diamond substrate (410). Optionally, the diamond substrate may be coated with a thin reflective or absorptive layer to prevent excitation light from reaching the fluidic layer (420). The fluidic layer (420) is formed on top of the implanted nitrogen-vacancy layer (415). The fluidic layer (420) may contain any number of receptacles, wells, or channels which contain and direct fluid. The optical assembly (425, 430, 440, 450) is constructed below the sensor chip (405). This allows clear access to the upper fluidic layer (420) for the deposition and manipulation of fluids for testing.

In this illustrative embodiment, excitation energy (435) enters the optical assembly from the side and is reflected upward by a beamsplitter (430) or dichroic mirror. For example, the excitation energy (435) may be green light. The beamsplitter (430) is constructed such that it reflects the green excitation light and transmits emitted red light. The green excitation energy passes upward through a first lens (425) which directs the light into the desired distribution on the implanted layer (415). As discussed above, the nitrogen-vacancy layer (415) emits a different and lower frequency of light. The characteristics of the emitted optical intensity depend on the presence or absence of magnetic fields and the frequency of an applied radio frequency (RF) field. According to one illustrative embodiment, the RF field is generated by an RF antenna (422) which is located in close proximity to the sensor chip (405). The emitted light (445) is collected by the first lens (425) and passes through the beamsplitter (430). A second lens (440) or lens assembly focuses the emitted light (445) onto an optical detector array (450) for imaging. The optical detector array (450) may be one of a number of detectors, including charge-coupled devices (CCD), complimentary metal-oxide-semiconductor (CMOS) sensors, and other devices. The optical detector array (450) images the photoluminescence intensity across the plane of NV centers.

According to one illustrative embodiment, a magnetic field source (426) may produce a DC magnetic field which is used to magnetize paramagnetic nanotags. The position and orientation of the magnetic field source (426) will differ for different applications. In applications where paramagnetic nanotags are not used, the magnetic field source (426) may be omitted. For example, when ferromagnetic nanoparticles are used, no magnetic field source (426) is needed.

The configuration shown in FIG. 4 is only one illustrative optical sensor system. A variety of other configurations could be used. For example, more complex optical designs could be used to provide more precise shaping and control of the optical beams. Alternatively, the optical detector array (450) may be placed very close to the implanted NV layer and image the emitted light without the use of optics. A filter may be formed over the optical detector array (450) to reject the excitation light (435).

FIG. 5 shows an alternative embodiment of a sensor system (500) in which the emitted light (545) from the sensor chip (505) is sensed from its upper surface. In this illustrative embodiment, the sensor chip (505) includes the fluidic layer (520), the implanted NV layer (515) and diamond substrate (510) as described above. A green excitation source (535) is included beneath the diamond substrate (510). The green excitation source (535) may include laser diodes, light emitting diodes, optical fibers which transmit light to the diamond substrate from an exterior source, or other light sources. The green light is transmitted upward through the diamond substrate to the implanted NV layer (515). The implanted NV layer (515) then generates emitted light (545) which is collected by a first lens (525). The emitted light (545) is separated from the green excitation light and other stray light by a filter (530). The second lens (540) focuses the emitted light (545) on a CCD array (550). Optionally, the diamond substrate may be coated with a thin reflective or absorptive layer to prevent excitation light from reaching the fluidic layer (520), while transmitting emitted light at longer wavelengths.

As described above, the CCD array may make multiple measurements of the emitted light (545) as the frequency of the RF energy is modulated. The output of the CCD array is monitored to detect band splitting, amplitude changes, or other variations in the emitted light which indicate the presence of an exterior magnetic field. This allows for real time sensing of magnetic material in the fluid.

FIGS. 6A-6E are diagrams illustrating one embodiment of functionalized NV surfaces which can be used to bind and then identify molecules using optically induced magnetic resonance. According to one illustrative embodiment, a multiplexed molecule assay can be made using a micro-fluidic sensor chip (600). The micro-fluidic sensor chip (600) includes a diamond chip (620) which has a well (605) formed on its upper surface. The well may be formed in a layer adhered to the diamond chip (620) or in the diamond chip (620) itself. Inside the well (610), an antibody microarray (610) is formed. According to one illustrative embodiment, the antibody microarray (610) includes a number of discrete areas, each of which contains a specific species of antibodies attached to the diamond substrate in that area.

Figure 6A:
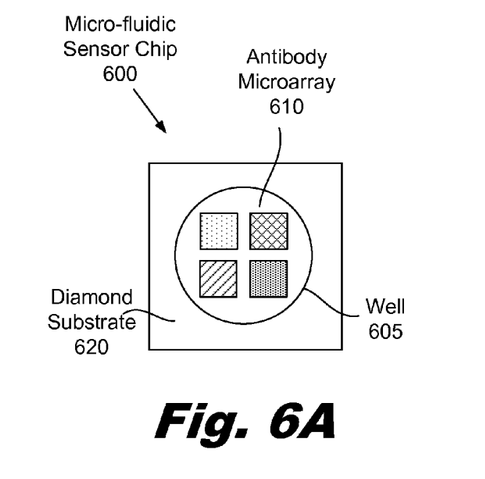
FIGS. 6A-6E are diagrams illustrating functionalization of nitrogen vacancy implanted surfaces to bind and identify molecules using optically induced magnetic resonance, according to one embodiment of principles described herein.
Figure 6B:
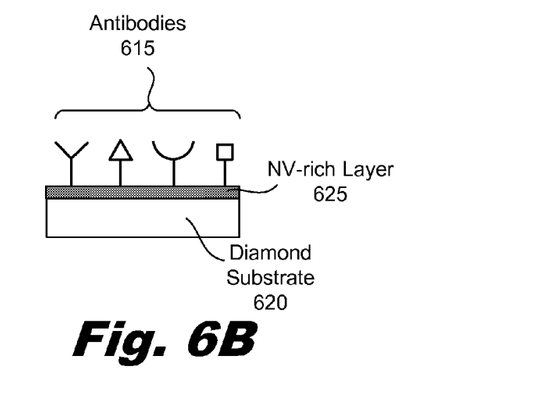

FIG. 6B is a side view of the illustrative microfluidic chip (600). The upper surface of the diamond substrate (620) is implanted with nitrogen-vacancies to form NV-rich layer (625). The various species of antibodies (615) are then attached (also called "functionalized") to the designated areas to form the antibody microarray (610). According to one illustrative embodiment, the sensor chip (600) may be configured to detect 50 or more analytes in a single well (605).

Figure 6C:
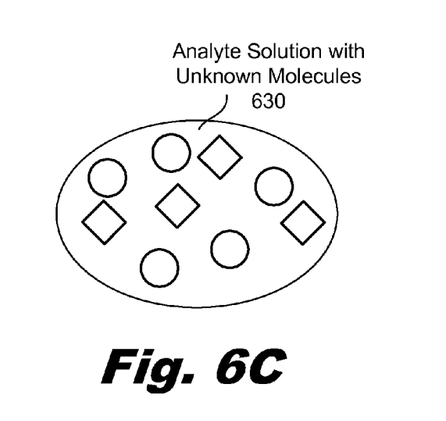

FIG. 6C shows an analyte solution (630) which includes a number of unknown molecules, proteins, or other constituents. This analyte solution (630) is introduced into the well (605). Through diffusion, the various molecules come into contact with the various antibodies (615) in the antibody microarray (610).

Figure 6D:
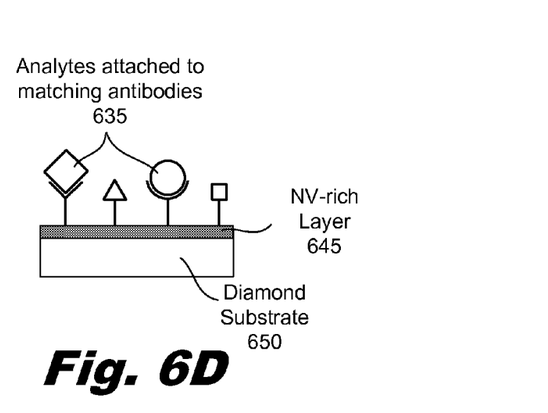
Figure 6E:
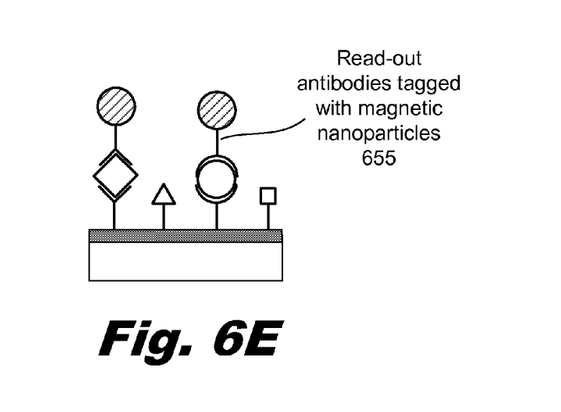

As shown in FIG. 6D, molecules (635) which match the various antibodies become attached to the antibodies and immobilized. The sample is then incubated with readout antibodies (655) which are tagged with magnetic nanoparticles, as shown in FIG. 6E. After the binding between the readout antibodies and the analytes is substantially complete, the excess magnetic nanoparticles are removed from the well (605). The use of magnetic nanoparticles eliminates the need of an additional rinsing step to wash away unbound tags. These can be removed from the sensing surface prior to the measurement by the application of a magnetic field. The presence of the remaining magnetic nanoparticles in each region of the antibody microarray (610) is then detected using ODMR to determine the concentrations of corresponding analytes.

The apparatus and method described above is only an illustrative example which describes one general process for detecting analytes with magnetic nanoparticles. A variety of variations and other methods could also be used. For example, a variety of intermediate molecules could be used in the process. According to one illustrative embodiment, detector antibodies could first be introduced and bound to the captured analytes. The magnetically tagged readout antibodies could then be introduced into the well. These magnetically tagged readout antibodies are configured such that they only bind to the detector antibodies.

According to one illustrative embodiment, the functionalized NV surfaces may be formed in the bottoms of microwells in an assay based device. As illustrated in the embodiments below, a variety of configurations could be used.

Figure 7:
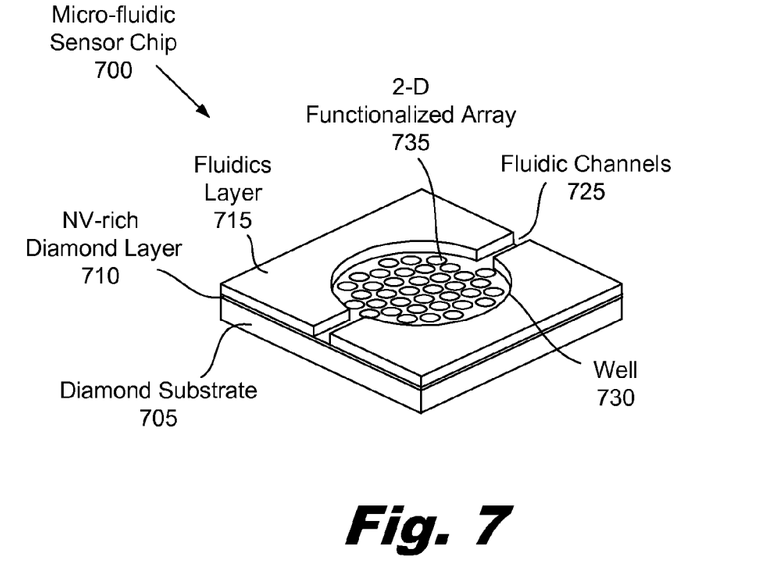
FIG. 7 is a perspective view of an illustrative micro-fluidic sensor chip, according to one embodiment of principles described herein.

FIG. 7 is an embodiment of an illustrative micro-fluidic sensor chip (700). In this illustrative embodiment, the diamond substrate (705) and nitrogen-vacancy rich diamond layer (710) are formed as described above. The fluidics layer (715) includes fluidic channels (725) and a well (730). The fluidic channels (725) feed fluid into the well (730), which serves as a reservoir to contain the fluid. According to one illustrative embodiment, the well (730) may serve as a reaction chamber which combines fluids which enter from the two or more fluidic channels connected to the well. As described above in FIGS. 6A-6E, a two dimensional functionalized array of antibodies (735) could be formed in the well (730). According to one illustrative embodiment, the array of antibodies (735) may be directly attached to the upper surface of the NV-rich diamond layer (710). This minimizes the distance between the nitrogen-vacancy centers and the magnetic nanoparticle tags.

The light emitted by the micro-fluidic sensor chip (700) could be detected using a variety of methods. For example, an optical sensor may be used to make two dimensional measurements of the emitted light. The optical sensor may be a CCD or other optical imaging device. FIGS. 4 and 5 show illustrative embodiments of sensor systems which could be used in conjunction with the microfluidic sensor chip (700).

Figure 8:
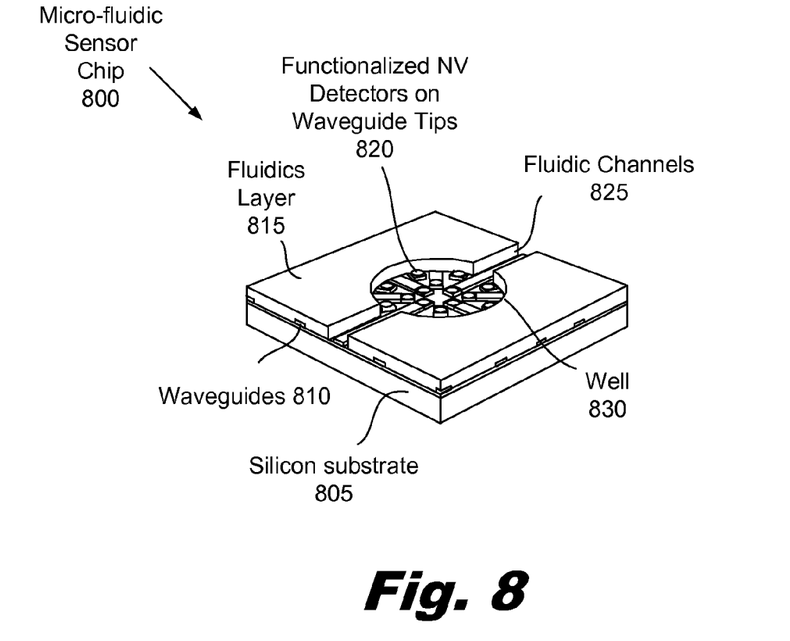
FIG. 8 is a perspective view of an illustrative micro-fluidic sensor chip, according to one embodiment of principles described herein.

FIG. 8 shows an illustrative micro-fluidic sensor chip (800) which has been constructed on a silicon substrate (805). A number of radially converging waveguides (810) are formed on the upper surface of the silicon substrate (805). The waveguides (810) terminate in a well (830). Fluid is fed into the well (830) through one or more fluidic channels (825). According to one illustrative embodiment, functionalized nitrogen-vacancy rich diamond is attached to the tip of each of the waveguides (810). The optical excitation energy passes through the waveguide (810) and is incident on the nitrogen-vacancy rich diamond material at the wave guide tip (820). According to one illustrative embodiment, the light emitted from the NV detector is transmitted back along the waveguide (810) to an optical sensor (not shown).

According to one illustrative embodiment, each waveguide tip may be functionalized such that specific biological molecules attach to selected waveguides. By magnetically tagging these molecules, the identity and concentration of the molecules within the fluid can be determined. For example, a magnetically tagged biological agent A may attach to the terminal end of a first waveguide and a magnetically tagged biological agent B may attach to the terminal end of a second waveguide. The changes in the emitted light generated by the nitrogen-vacancy rich diamond material deposited on the ends of the first and second waveguide is then analyzed to detect the presence and amount of agents A and B.

Additionally or alternatively, the light emitted by the NV detector may be detected by an imaging focal plane array such as a CCD array. When a magnetic field is produced near one or more of the tips of the waveguides (810), the magnitude and possibly the direction of the magnetic field can be sensed through alterations in the emitted light.

According to one illustrative embodiment, the sensor chips may be shielded from stray magnetic fields. These stray magnetic fields may include the earth's magnetic field, magnetic fields produced by electronic devices or wiring, and permanent magnets. In some embodiments, the sensor chips may be used in a controlled laboratory environment where many of these magnetic fields can be eliminated. For use in the field, the sensor chips may be shielded by using high magnetic permeability metal alloys or by superconducting materials which expel magnetic fields via the Meissner effect.

In other situations, all or a portion of the stray magnetic fields may be calibrated out of the measurements. For example, a calibration procedure may include making measurements from two substantially identical optically integrated magnetic detectors. The two detectors may be relatively close together so that both detectors are sensing the same stray magnetic fields. However, only one detector senses the magnetically tagged molecules in the test fluid. By differencing the measurements of the two detectors, the effects of the stray magnetic field may be cancelled out.

Figure 9:
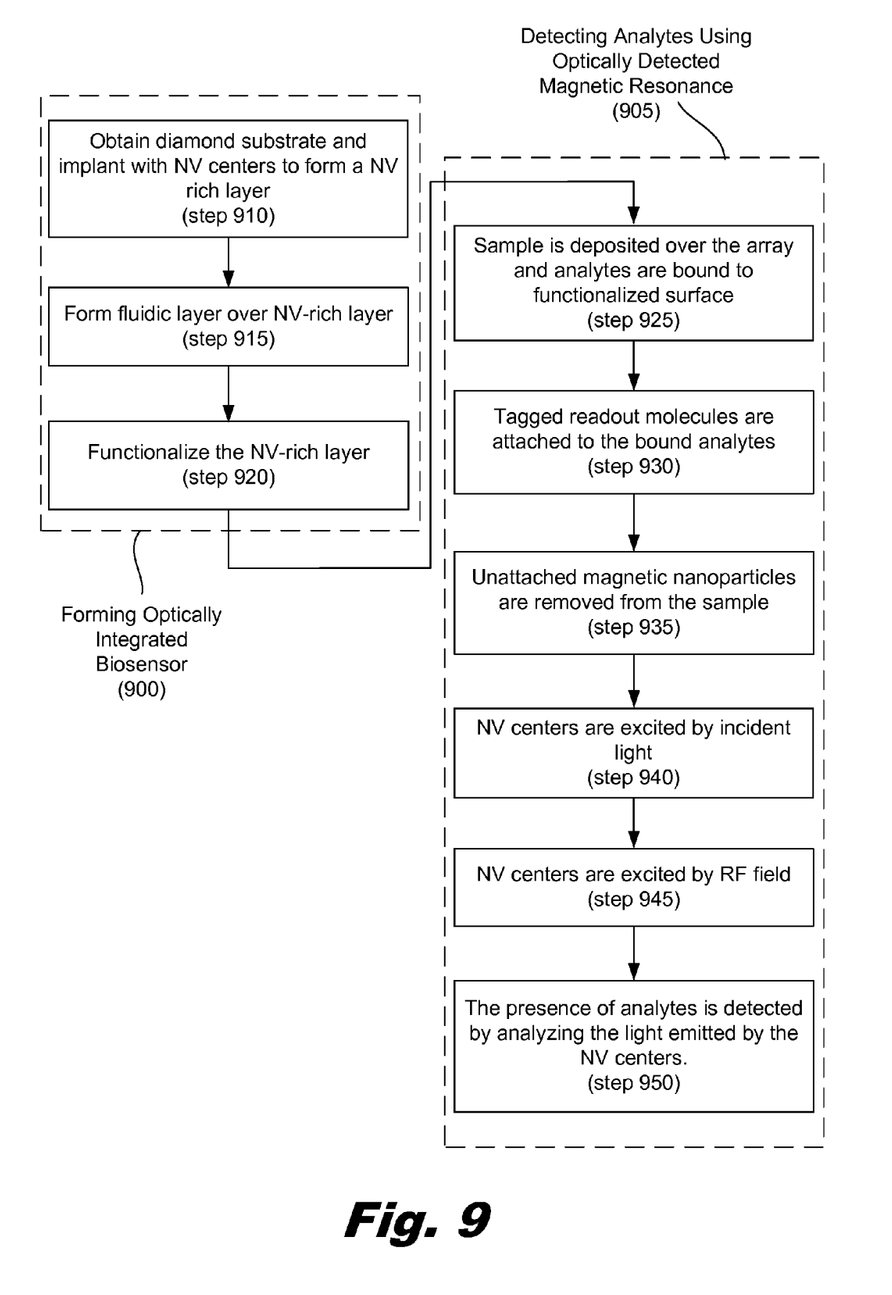
FIG. 9 is a flow chart describing an illustrative method for detecting magnetic bio-tags, according to one illustrative embodiment of principles described herein.

FIG. 9 is a flow chart which describes an illustrative method for forming an optically integrated biosensor (900) and using the sensor to detect analytes using optically detected magnetic resonance (905). In a first step, a diamond substrate is obtained and implanted with NV centers to form a NV-rich layer (step 910). Additionally or alternatively, NV implanted nanoparticles could be distributed over a surface to create the desired ODMR behavior within the device.

Over the NV-rich layer, a fluidic layer is formed (step 915). The fluidic layer may have a variety of geometries which contain and direct fluid, such as channels and wells. Portions of the NV-rich diamond surface are then functionalized to produce a microarray (step 920). Various sections of the microarray may be configured to bind specific analytes or families of analytes. According to one illustrative embodiment, the optically integrated biosensor can be readily integrated into conventional microwells and leverage existing assay equipment and techniques.

A sample is deposited over the microarray (step 925). The sample may contain a variety of known and/or unknown molecules. The molecules which match one or more sections of the microarray attach to that surface. According to one illustrative embodiment, the unknown molecules are proteins and the NV surface is functionalized with various antibodies. As the sample is deposited on the microarray, the functionalized antibodies are bound to the antibodies.

Tagged readout molecules which include magnetic nanoparticles are then attached to the bound analytes (step 930). Because the analytes and tagged readout molecules can be bound to the antibodies or other functionalized molecules with a high degree of specificity, the analytes can be accurately identified. Additionally, the magnetic nanoparticles are brought within nanometers of the NV rich surface by the binding process. This allows the nanoparticles to be more easily detected.

According to one illustrative embodiment, readout molecules are first attached to the bound analytes, and then the magnetic nanoparticles are added. The magnetic nanoparticles then preferentially bind to the readout molecules. In some embodiments, the surface magnetic nanoparticles may be modified by attaching a biologically active molecule which binds with the readout molecule.

After a substantial number of the magnetic nanoparticles have been attached to the readout molecules, the unattached magnetic nanoparticles are removed from the sample (step 935). According to one illustrative embodiment, the magnetic nanoparticles can be removed from the sample by applying an external magnetic field. Additionally or alternatively, the unbound analytes and magnetic nanoparticles may be removed by flushing them off of the microarray surface.

The NV centers are then excited with light having the appropriate frequency or range of frequencies (step 940). For example, the NV centers may be illuminated with green laser light which excites electrons from a ground state to an excited state. Additionally, the NV centers are exposed to an RF field (step 945). According to one illustrative embodiment, the RF field emitted by the radio frequency transmitter is scanned through frequencies which correspond to ground state transitions of the nitrogen-vacancy centers. Additionally or alternatively, the RF field may be centered on a frequency which corresponds to a ground state transition of a background magnetic field.

The presence and amount of analytes bound to specific regions of the microarray can then be detected by changes in the emitted light from the NV centers as they are simultaneously exposed to the optical and RF excitation (step 950). According to one illustrative embodiment, the emitted light may travel through an optical filter to an optical detector, which converts the photon emissions into an electrical signal. The electrical signal is analyzed to determine if changes in the emitted optical intensity indicate the presence of an exterior magnetic field. In some circumstances the electrical signal may be calibrated to reduce the effects of stray optical and magnetic energy. According to one illustrative embodiment, the optically detected magnetic resonance technology is configured to detect single magnetic nanoparticles less than 20 nanometers in size with magnetic moments of approximately $10^{-15}$ emu. In addition to increased sensitivity, the ODMR based biosensor can reduce the time and number of steps involved in the assay procedure.

In sum, diamond substrate implanted with nitrogen-vacancy centers serves as a highly sensitive two dimensional detector of magnetic nanotags. According to one illustrative embodiment, the sensor is easily integrated with a microfluidic chip and can be reused indefinitely.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. An optically integrated magnetic biosensor based on optically detected magnetic resonance (ODMR) comprises:
    an ODMR center;
    a fluidics layer configured to contain a solution comprising analytes, the fluidics layer being disposed over the ODMR center;
    a light source configured to generate incident light which excites electrons within the ODMR center from a ground state to an excited state; and
    a radio frequency (RF) antenna configured to generate an RF field incident on the ODMR center, the RF antenna being further configured to generate the RF field with frequencies which correspond to ground state transitions in the ODMR center;
    in which the ODMR center produces emitted light when illuminated by the incident light, characteristics of the emitted light being influenced by the RF field and magnetic nanoparticles attached to the analytes.

2. The sensor of claim 1, further comprising a functionalized surface in proximity to the ODMR center, the functionalized surface being configured to selectively attach to the analytes.

3. The sensor of claim 2, in which the fluidics layer comprises a plurality of fluid wells, at least one ODMR center being disposed in proximity to each of the plurality of fluid wells.

4. The sensor of claim 2, in which the functionalized surface comprises an array of functionalized areas, each functionalized area being configured to selectively bind to a class of analytes.

5. The sensor of claim 1, further comprising an optical blocking layer, the optical blocking layer being reflective or absorptive over a range of optical wavelengths such that at least a portion of the incident light is blocked from passing into the fluidics layer.

6. The sensor of claim 1, in which the ODMR center is a nitrogen-vacancy center in a diamond lattice.

7. The sensor of claim 6, in which a plurality of ODMR centers is formed in an upper surface of a diamond substrate.

8. The sensor of claim 1, further comprising an optical waveguide, the optical waveguide being configured to convey the incident light to the ODMR center and convey the emitted light to an optical detector.

9. The sensor of claim 8, in which the ODMR center is disposed on a terminal end of the optical waveguide.

10. The sensor of claim 8, in which a plurality of optical waveguides terminate in a fluid well.

11. The sensor of claim 1, in which the ODMR center is a nitrogen-vacancy center within a diamond layer, an exterior surface of the diamond layer being biologically functionalized.

12. The sensor of claim 2, further comprising a bonding layer configured to adhere the fluidic layer to a substrate containing ODMR centers.

13. The sensor of claim 1, further comprising:

an optical detector;

a filter configured to separate the emitted light from the incident light and transmit the emitted light to the optical detector.

14. The sensor of claim 13, in which the optical detector is an optical detector array configured to image a two dimensional surface of a layer containing multiple ODMR centers.

15. The sensor of claim 1, in which a layer containing multiple ODMR centers is sandwiched between a substrate and a fluidic layer, the fluidic layer containing the fluid.

16. The sensor of claim 15, in which the incident light passes through the substrate and illuminates the multiple ODMR centers, the emitted light being sensed through the fluidic layer.

17. The sensor of claim 15, in which the incident light passes through the substrate and illuminates the multiple ODMR centers, the emitted light being sensed through the substrate.

18. A method for detecting analytes comprises:

depositing a sample over a functionalized array, the functionalized array being formed on a surface containing ODMR centers, analytes within the sample selectively binding to portions of the functionalized array;

attaching readout molecules to analytes bound to the functionalized array, the readout molecules being tagged with magnetic nanoparticles;

exciting the ODMR centers with incident light and an RF field; and detecting the presence of analytes bound to the functionalized array by analyzing light emitted by the ODMR centers.

19. The method of claim 18, further comprising scanning the frequency of the RF field to pass through the ground state transitions of the ODMR centers.

20. The method of claim 19, further comprising centering the RF energy frequency which corresponds to a ground state transition of a background magnetic field.

* * * * *